United States Patent
Jaffe

(12) 
(10) Patent No.: US 6,632,622 B2
(45) Date of Patent: Oct. 14, 2003

(54) ASSAY FOR EVALUATION OF CELLULAR RESPONSE TO ALLERGENS

(76) Inventor: Russell Jaffe, 10430 Hunter View, Vienna, VA (US) 22181

(*) Notice: Subject to any disclaimer, the term of this patent is extended or adjusted under 35 U.S.C. 154(b) by 0 days.

(21) Appl. No.: 09/832,343

(22) Filed: Apr. 11, 2001

(65) Prior Publication Data

US 2002/0187516 A1 Dec. 12, 2002

Related U.S. Application Data

(63) Continuation-in-part of application No. 08/253,744, filed on Jun. 3, 1994, now abandoned, which is a continuation-in-part of application No. 07/910,877, filed on Jul. 10, 1992, now abandoned.

(51) Int. Cl.$^7$ ................................................ G01N 33/53
(52) U.S. Cl. ................ 435/7.24; 436/517; 436/518; 436/513; 422/68.1; 424/534; 424/520; 435/23; 435/29; 435/7.1; 435/7.2
(58) Field of Search .................. 436/513, 518, 436/517; 435/7.1, 23, 724, 7.2, 29; 422/68.1; 514/2; 424/534, 520

(56) References Cited

U.S. PATENT DOCUMENTS

| | | | | |
|---|---|---|---|---|
| 4,225,575 A | * | 9/1980 | Piasio et al. | 424/1 |
| 4,318,886 A | * | 3/1982 | Kawahara et al. | 422/68 |
| 4,592,997 A | * | 6/1986 | Wilhelms et al. | 435/23 |
| 4,666,834 A | * | 5/1987 | Bekesi et al. | 435/29 |
| 4,735,778 A | * | 4/1988 | Maruyama et al. | 422/102 |
| 4,920,097 A | * | 4/1990 | Gottlieb et al. | 514/2 |
| 5,476,797 A | * | 12/1995 | Matsunaga | 436/513 |

* cited by examiner

*Primary Examiner*—Long V. Le
*Assistant Examiner*—Deborah A Davis
(74) *Attorney, Agent, or Firm*—Morrison & Foerster LLP

(57) ABSTRACT

An assay method for detecting the response or activation of cells, including lymphocytes, and a method for detecting immunological sensitization in a subject, which involves the introduction of cell-activating substance which causes an enzyme of the cells to become available for reaction, and the measurement of the enzymatic reaction using a substrate which generates a detectable product, and a kit for performing such assays.

5 Claims, 1 Drawing Sheet

ASSAY FOR EVALUATION OF CELLULAR RESPONSE TO ALLERGENS

REFERENCE TO RELATED APPLICATIONS

This application is a continuation-in-part of U.S. Ser. No. 08/253,744 filed Jun. 3, 1994, now abandoned, which is a continuation-in-part of U.S. Ser. No. 07/910,877 filed Jul. 10, 1992, now abandoned.

FIELD OF THE INVENTION

This invention is in the field of diagnostic immunology. The invention provides means of identifying response of living patient cells to specific antigens as a means of identifying hypersensitivity and evaluating effects of regimens used to treat allergic responses. Another aspect of the invention is improved plates which are particularly useful for practice of the inventive process.

BACKGROUND OF THE INVENTION

The evaluation of immune responses in patients presenting with clinical symptoms of allergic response presents many problems. While skin testing may be helpful, such testing has not provided an effective tool for evaluation of changes in immune response during treatment.

Since the 1960's, numerous in vitro assays have been used to augment in vivo evaluation of immune response. Many of these bioassays are based on understanding of effect of antigenic substances on lymphocytes. Many of the tests evaluate lymphocyte proliferation in the presence of appropriately presented antigens require use of radioactive materials such as $^3$H-thymidine or [$^{125}$I]iododeoxyuridine for evaluation of changes in cell activation. These assays require specialized equipment and Ye relatively expensive to perform. The tests of the prior art usually require 3–7 day's time. Results are not as reliable as would be desired.

Ulf Landegren (*J. Immunol. Meth.* 67 379–388 (1984)) developed an assay to measure lymphocyte proliferation wherein he used a chromogenic indicator, p-nitrophenol-N-acetyl-β-D-glucosaminide. The absorbance at 405 nm ($A_{405}$), when read using a colorimetric plate reader, indicated the amount of color generated was directly proportional to the cell number.

Tim Mosmann (*j. immunol. meth.* 65: 55–63 (1983)) developed an assay using tetrazolium salt MTT (3-(4,5-dimethylthiazol-2-yl)-2,5-diphenyl tetrazolium bromide) to measure mammalian cell survival and proliferation. The assay detects living cells. The response is dependent on the degree of activation of the cells. The method was used to measure proliferative lymphokines, mitogen stimulations and complement-mediated lysis. Using the tetrazolium salt as an indicator, it was found that the absorbance readings indicated a linear relationship between cell number and color formation.

Wilhelms, U.S. Pat. No. 4,592,997 teaches a method for evaluation of leukocyte activation by incubation of cells with allergens followed by measurement of protease liberation wherein a chromogenic substrate is used as the colorimetric indicator.

Hashimoto, et al. (*J. Immunol. Meth.* 90: 97–103 (1986)) taught use of an assay to detect B-cell proliferation using chromogenic indicators of intracellular enzymes such as APase. His teaching shows no evidence of activation prior to 3 days of exposure to the activating agent.

Chan, et al. (*Anal. Biochem.* 157: 375–380 (1986)) describes a direct colorimetric assay for measuring $Ca^{2+}$-stimulated ed ATPase activity on adipocyte plasma membrane preparation. The enzyme was measured in cell extracts.

SUMMARY OF THE INVENTION

Figure 1:
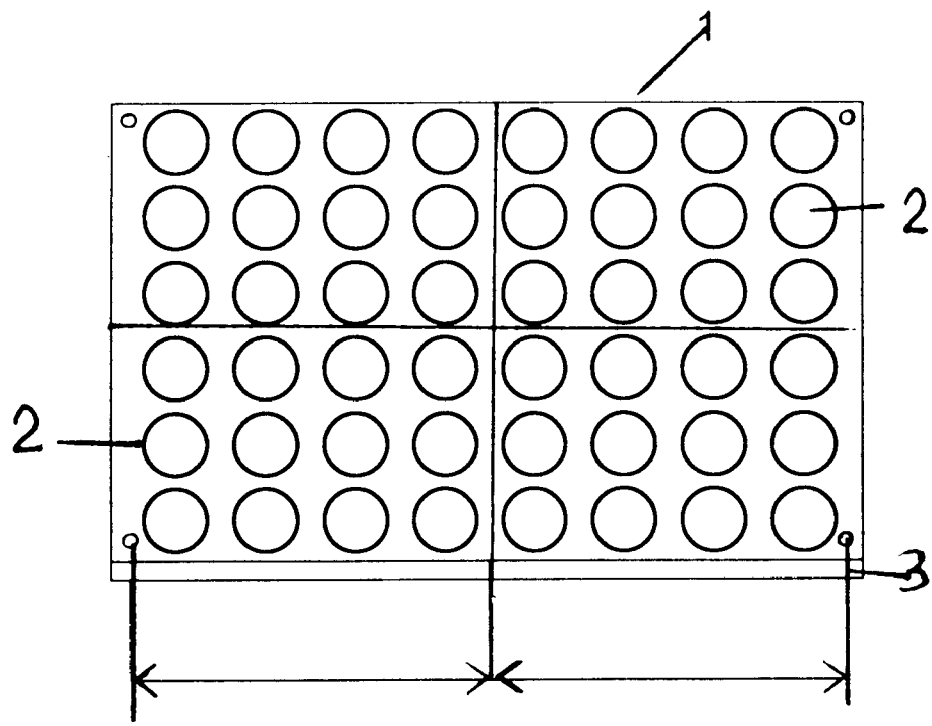
FIG. 1 is a drawing of a plate having 48 wells.

The instant invention provides an assay for evaluation of allergic response by exposure of leukocyte-rich plasma to multiple samples of antigens under incubation for less than 6 hours followed by evaluation of reactive response of the leukocytes. The assay is rapid, simple, requires a relatively small amount of blood, and avoids use of radioisotopes. While colorimetric indicators may be used in the inventive method, such indicators are not needed. The method of the invention requires little handling of the cells, can be automated, and provides readily reproducible results.

The method of the invention requires (a) bringing cells capable of activation into contact with an antigenic substance for a suitable interval and under conditions which encourage an enzymatic response in the cell followed by (b) examining the cells and plasma to detect evidence of cell activation. It is also possible, during step (a), to provide a color indicator that will respond to enzyme production by changing light absorbance of the cells or substrate in which the cells are suspended (usually plasma).

The method provides a means of evaluating hypersensitivity by exposing leukocytes to antigens. A leukocyte-rich plasma is prepared from patient's uncoagulated blood. The leukocyte-rich plasma is then exposed to antigen bound to wells of a multi-welled plate. The plates are then incubated for a sufficient period of time to facilitate activation of any leukocytes sensitive to the antigen in the well. Each well of the plate is then inspected to determine if the leukocytes show evidence of activation by the antigen in the particular well.

The antigens used in the assay include foods, common environmental antigens, food additives, hydrocarbons (including commonly used solvents), and household cleaning materials.

By methods of the invention, it is possible both to identify substances to which patients are allergic and to evaluate the patient's response to therapy.

The use of plates having flat bottoms facilitates the evaluation of cellular response. Kits containing several plates with different antigens bound thereto may be supplied for use in accord with the methods of the invention. Such plates may be coated with allergens.

DETAILED DESCRIPTION OF THE INVENTION

The assay of the invention requires the collection of blood under conditions that prevent clotting. The cells are handled as little as possible. With minimal handling, the blood samples are subjected to separation means, usually by carefully controlled centrifugation, to provide a leukocyte-rich supernatant. During the activation process described herein enzymes become available on and near the surface of the cell which cause change in volume and membrane characteristics of the cell. When a color indicator is used, the enzymes released by the cells react with the color indicator to decrease absorbance of light.

A preferred method of the invention employs the use of multiply-compartmented flat-bottomed plates wherein the bottom surface of the wells is optically plane and wherein each compartment is coated with a different antigen. Leukocyte-rich plasma is then added to the compartments. A color indicator may be added to the plasma before the plasma is added to the compartments of the plates. The plates are then incubated for a period of time sufficient to permit activation of the leukocytes by antigens. A close correlation between cellular response and clinical response to allergens to which the individual is sensitive has been shown. Incubation for at least 0.5 hours is usually required. The optimum time for incubation is about 1.5 to 4 hours. At present, the preferred practice is to incubate 2.5 to 3 hours.

After incubation of the plates, the plates are read in a microtiter plate reader. The activated cells will, after incubation, appear enlarged and a halo effect will be noted at the edge of the cells. If a chromogenic indicator has been added, the activation of the cells will be indicated by a fall in absorbance of light. When an indicator is used, tetrazolium salts are a preferred class for use in the methods of the invention.

The antigens usually used in the methods of the invention include those shown in Table I.

TABLE I

| CATEGORY | EXAMPLES OF ANTIGENS |
|---|---|
| A: Foods: | |
| 1. Crustacean/Mollusk | crab, lobster, shrimp, clam oyster, scallop |
| 2. Dairy | butter, cheese, milk, casein, yogurt |
| 3. Fish | anchovy, bass, catfish, codfish, haddock, perch, mackerel, red snapper, salmon, sardine, sole, flounder, halibut, swordfish, trout, tuna, turbot, whitefish |
| 4. Fowl | chicken, goose, duck, turkey, pheasant, quail, and other game birds. |
| 5. Fruit | apple, apricot, banana, berries (blackberry, blueberry, boysenberry, cranberry, raspberry, strawberry), cherry, coconut, currant, date, fig, grape/raisin, grapefruit, kiwi, lemon, lime, orange, tangerine, mango, melon (cantaloupe, honeydew, watermelon), nectarine, papaya, peach, pear, pineapple, plum, tamarind. |
| 6. Grain/seeds | barley, buckwheat, corn, millet, oats, rice, rye, wheat, wild rice, alfalfa, anise, poppy seed, pumpkin,, sesame, sunflower |
| 7. Meat | beef/veal, lamb/mutton, pork, deer, moose, rabbit, goat |
| 8. Nuts | almond, brazil nut, cashew, chestnut, hazelnut, macadamia, peanut, pecan, pine, pistachio, walnut |
| 9. Oils | cod liver oil, corn, cottonseed, hazelnut, linseed, olive, peanut, primrose, safflower, sesame, sunflower, walnut |
| 10. Spice | allspice, arrowroot, bay leaf, caraway seed, chili pepper, cinnamon, clove, dill, ginger, horseradish, mace, mustard, nutmeg, oregano, paprika, pepper (black, cayenne, white), peppermint, rosemary, sage, basil, spearmint, thyme, vanilla |
| 11. Vegetable | artichoke, asparagus, avocado, beans (black-eyed peas, chick pea, kidney, lima, navy, pinto, soya, string, wax), beet, broccoli, brussels sprout, cabbage, carrot, cauliflower, celery, corn, cucumber, eggplant, garlic, lentil, lettuce, mushroom, olive, onion, parsley, parsnip, red pepper, green pepper, pimento, white potato, sweet potato, radish, rhubarb, rutabaga, spinach, squash, turnip, watercress cassava, malanga, kale. |

TABLE I-continued

| CATEGORY | EXAMPLES OF ANTIGENS |
|---|---|
| MISCELLANEOUS | algae, coffee, cocoa, cola, juniper berries, hops, yeasts, kelp, malt, psyllium seed, rose hips, tapioca, tea, tobacco, formaldehyde, caffeine, coal tar, detergents, pesticides, metallic catalysts, organophosphates, petroleum byproducts, soaps |
| FOOD ADDITIVES & PRESERVATIVES | Aspartane, BHT, BHA, food colorings, MSG, saccharine, benzoate, sulfites, nitrates, baking powder, baking soda |
| DRUGS | antibiotics (penicillins, tetracyclines, erythromycin, cyclosporins), salicylate |

Color indicators used are those that are known to be acted upon by an enzyme produced during cell activation to provide color to the substrate. The coloration results in a fall in absorbance at the appropriate wave-length of the medium in which the reaction takes place. In the instant case, the medium used was plasma. When the tetrazolium salt is used as indicated in the example, the typical changes in 35 $\mu l$ of cell rich plasma containing 30,000±500 blood cells is a decrease in absorbance of 1.100±0.005 units in the presence of an activating agent compared with a background decrease of 0.001±0.0005 units (based on starting absorbance of 0.150 units) in the cell-rich plasma wherein the cells have not been activated. Such a variation can be observed when the plates are read on a standard 96-well microtiter plate reader.

While various receptacle-containing plates can be used as support matrix and reaction vessels, including polystyrenes, acrylonitriles, polycarbonates, polypentenes, or glass. However, by far the preferred material is virgin optical styrene (optical grade polystyrene).

The shape of the reaction vessel is important. The vessel is designed to optimize physiological response. The vessel must be constructed in such a manner that adequate exchange of gasses (oxygen and $CO_2$) occurs. The vessels must facilitate rapid pH equilibration and diffusion of molecules and provide for ample dissipation of heat that might result from reactions or exposure to extraneous heat. Standard microtitration plates are not appropriate for practice of the invention. The reaction vessel must have the following features:

(1) The ratio of surface (mm) to sample volume ($\mu l$) must be greater than or equal to 0.1.

(2) The preferred diameter is about 6 mm and the preferred sidewall height is about 0.5 to about 6 mm. A height of 1<2 mm is most preferred.

In the preferred embodiments, the reaction vessels are arranged as plates having 48 or 96 wells. This arrangement makes it possible to examine the plates using a microtiter plate reader. The reaction vessels, in addition to being much more shallow than those of standard microtiter plates, are made with flat bottoms. The plates of the invention are best made by injection molding, so the entire bottom surface of the plate is one flat surface. The vessels of the plates are flat on the bottom and have 90° angles at the juncture where the sides and bottoms of the vessel meet.

Figure 2:
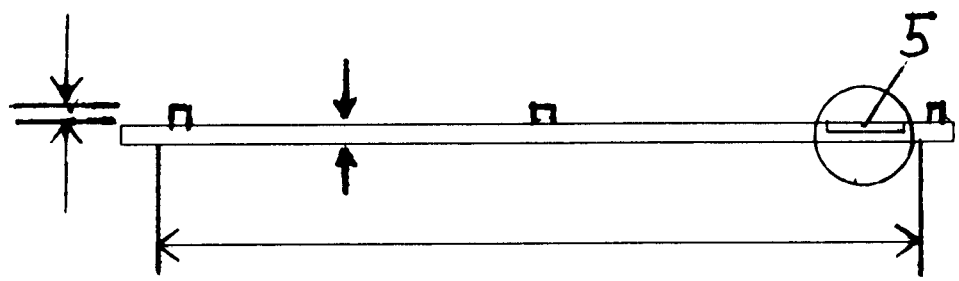
FIG. 2 shows a cross-section view of the plate with the well.
Figure 3:
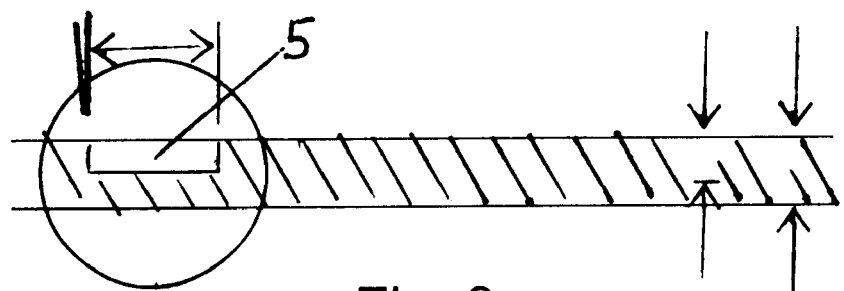
FIG. 3 shows a cross section of the plate with the well.

Referring to the figures, FIG. 1 shows a plate (1) having wells (2) and a beveled side (3). FIG. 2 shows a side view of a plate with a cross section of a well (5) at one end. FIG. 3 shows a small portion of the plate with the well in cross section. The plate should provide an optically plane surface against which to view the cells. The plates should be essentially unclouded and transparent.

As indicated previously, minimal handling of the samples is desirable, since handling of the cells can cause stress that will give false positive reactions. Hence, careful centrifugation of un-coagulated blood to provide a leukocyte-rich plasma facilitates accurate evaluation of allergic response. The method of preparation exemplified herein is particularly useful for obtaining accurate information regarding hypersensitivity response.

EXAMPLE 1

Preparation of the Leukocyte-rich Plasma

Samples of blood (about 30 ml.) were drawn into tubes that contained anticoagulant. (For example, collection tubes may be prepared using 3 ml 3.8% citrate solution. The sodium, potassium, magnesium salts are preferred.) The uncoagulated blood was centrifuged for a total of 980 gmin$^{-1}$. After centrifugation, 3 ml of supernatant was removed from the sample using a transfer pipette by allowing the transfer pipette to follow the liquid level down the tube. This sample contained leucocyte poor plasma (LPP), and was reserved. The remaining plasma, richer in leukocytes, was then carefully removed by transfer pipette to avoid interruption of the plasma-red cell interface. The lymphocyte-rich plasma (LRP) was aspirated using a plastic transfer pipet. (If the plasma-red cell interface is disturbed, the plasma should be carefully allowed to return to the sample tube, and the sample should be re-centrifuged.)

EXAMPLE 2

Testing of Leukocyte-rich Plasma

The plates were prepared in racks made by Sandy Springs Instrument Company of Ijamisville, Md. (model 96-200). A different antigen solution of 0.04±0.005 ml/well was dispensed pensed into each receptacle on the plate. The plates were then dried.

Aliquots of 35 µl of the leukocyte-rich plasma were then transferred to each well of the plate prepared as indicated above. The plates were covered and incubated for 3 hours at 35°±2.00° C.

Within 30 minutes after removal from the incubator, the slides were placed in a microtiter plate reader. Numerous fields in each well were examined using a binocular microscope using a 35×power, aplanal, achromatic 40×LWD under monochromatic light. The background of each well appeared relatively amorphous. The color of the background varies depending on the color extractible from the original antigen. Most antigens presented a uniform dull-gray, amorphous appearance.

In reactive cells, the following factors were noted:
(1) a pale, blue-gray appearance of the cytoplasmic and nuclear material of the leucocyte;
(2) distinct and uniform halo (colorless to pale blue-gray) around the leucocyte, most readily observed by focusing above, through and below the individual leucocyte; and
(3) uniform distribution of reactive leucocytes in the well (70%–100% per counted cells/microscope field). Leucocyte distribution may be non-uniform near the edge of the well. Hence, the reader should avoid reading cells at the edge of the well.

Reactions called herein "false positives" may, at the cellular level, demonstrate some of the characteristics of a positive cell. The internal appearance of the leukocyte may have the pale, blue-gray color, but the halo characteristic of the false positive, if present, is not uniform around the cell in the case of the "false positive" reaction. Furthermore, in instances of fields containing less than 25%–30% "haloed" cells are considered non-positive.

EXAMPLE 3

Use of Chromogen in the Test

The sample was prepared in accord with Example 1. However, to the cell-rich plasma was added a mixture containing tetrazolium blue in a concentration of 500 pmoles diluted in 10 µl cell-poor plasma. The plates were then prepared and incubated in accord with the method of Example 2. Cell activation was assessed as enzyme activity measured as a rise in color of the plasma. Absorbance was read at 340 nm or 340/380 nm on a BioRad Model 1500 plate reader.

The results following a 3 hour incubation at 35±1° C. were as follows:
(1) the average intracellular absorbance ($A_{340}$) of leukocytes increased from a background of 0.204±0.008 to 1.954±0.051 units in the activated cells;
(2) absorbance of the plasma decreased by about 0.115 units (from 115±0.001 to 1.385±0.002 units) during this incubation; and
(3) apparent cell volume for CD4-positive T lymphocytes increased from 6.4±0.2µ to 7.9±0.22µ (N=400, p<0.00.)

EXAMPLE 4

Results

Determination of Predictive Value of Tests

To determine the predictive sensitivity and specificity of the assay using food and chemical allergens in detection of late-phase or delayed hypersensitivity, results were classified according the subjects' self-report of symptom frequency using a standard symptom questionnaire, the Cornell Medical Index (CMI$^R$). As shown below, subjects with few symptoms demonstrated ed few reactions. The test data showed increasing numbers and intensity of cellular reactions as the symptoms of reported by the patients became more numerous and severe.

| No. of symptoms (CMI) | Positive Test Responses |
| --- | --- |
| 0 | .06 ± 0.5 |
| 1–10 | 3.7 ± 0.9 |
| 11–20 | 5.8 ± 1.1 |
| 21–30 | 9.2 ± 1.2 |
| >31 | 18.4 ± 8.4 |

To determine the effectiveness of using this assay under clinical conditions, a research follow-up was conducted on a group of 94 subjects wherein assays were repeated at 6 month intervals. On repetition, it was shown that as the patient's symptoms decreased, the number of substances to which the individual reacted decreased. It was shown thereby that the effectiveness of treatment can be tracked by the use of the methods of the invention. Hence, the method is deemed valuable for clinicians tracking the progress of their patients.

EXAMPLE 5

Follow-up Studies

Forty-one patients underwent 102 individual tests with retests spread over a period of 7 to 32 months. Patients were instructed to abstain from contact with food and chemical agents to which they tested positive for hypersensitivity in the initial assay. Comparison of the reactions for each individual before treatment and after treatment were evaluated. Data regarding the frequency of response to particular agents and the number of total positive reactions were considered. Results:

The average reduction in positive reactions between the first and last tests show that the number of strong reactions were reduced by an average of 62%. Initially the average number of strong reactions was seen to 29 of the 180 allergens tested. On retest the average number of strong reactions dropped to 11. When milder reactions (fewer cells showing reactivity) were evaluated, the average number of intermediate reactions increased from 11.3 to 18.2. This change was attributed to the decreasing intensity of hypersensitivity among the subjects. In some cases new reactions were seen as the patient changed his or her diet. This phenomena was believed to account for a small portion of the increased number of intermediate reactions. While clinical improvement was often noted before detectable change in the cellular response as evaluated by the test of the invention, the test data proved useful in many cases as a means of identifying both general improvement and in identifying more particularly the antigens most likely to cause cellular response in the patient.

The effect of modification of diet and exposure to environmental allergens over time was evaluated. Treatment of all patients commenced after the initial testing. The patients were grouped into three categories: Those who were retested 7–12 months after initial testing, those who were retested 13–18 months after initial testing, and those retested more than 19 months after initial testing. In patients tested within the first 6 months after initial testing, a modest (3%) decrease in total number of positive reactions was observed.

A shift from a state of hypersensitivity as indicated by cellular response in the assay appeared to required several months. Patients studied typically had 3 to 20$^+$ years of impaired function and multiple, marginally successful or unsuccessful responses to treatment. Preliminary data indicates that the majority of reactions can be completely eliminated with careful modification of the patient's diet or environment as indicated necessary by the test data.

What is claimed is:

1. A method of evaluating hypersensitivity of leukocytes to antigens in the absence of a chromogenic indicator comprising the steps of:

(a) introducing leukocyte-rich plasma in the absence of a chromogenic indicator into wells of multiwell plates wherein the bottoms of said wells of said plates provide an optically plane surface and wherein said wells have said antigens bound thereto;

(b) incubating said plates for a sufficient period of time to activate the leukocytes in said wells which are sensitive to said antigens; and (c) examining said plates in a microtiter plate reader for evidence of activation, the evidence sought being a pale, blue-gray appearance of cytoplasmic and nuclear material of the leukocyte, a distinct and uniform halo that is colorless to pale blue around the leukocyte, and a uniform distribution of reactive leukocytes in the well, to identify wells having antigen bound thereto containing leukocytes which show evidence of activation.

2. The method of claim 1 wherein the multiwell plates comprise virgin optical styrene.

3. The method of claim 1 wherein the sides and bottom of the wells meet at a 90° angle.

4. The method of claim 1 wherein the incubation period is 1.5 to 4 hours.

5. The method of claim 1 wherein the incubation period is 2.5 to 3 hours.

* * * * *